US010175221B2

(12) United States Patent
Ciampini

(10) Patent No.: US 10,175,221 B2
(45) Date of Patent: Jan. 8, 2019

(54) DETECTION DEVICE TO IDENTIFY MARKERS DISSOLVED IN A LIQUID BY MEANS OF A MEASUREMENT OF RESISTIVITY VARIATION, DETECTION METHOD AND USE OF MARKER AND DETECTION DEVICE

(71) Applicant: SICPA HOLDING SA, Prilly (CH)

(72) Inventor: Davide Ciampini, Pavone Canavese (IT)

(73) Assignee: SICPA HOLDING SA, Prilly (CH)

( * ) Notice: Subject to any disclaimer, the term of this patent is extended or adjusted under 35 U.S.C. 154(b) by 158 days.

(21) Appl. No.: 15/328,370

(22) PCT Filed: Sep. 25, 2015

(86) PCT No.: PCT/EP2015/072108
§ 371 (c)(1),
(2) Date: Jan. 23, 2017

(87) PCT Pub. No.: WO2016/050635
PCT Pub. Date: Apr. 7, 2016

(65) Prior Publication Data
US 2017/0219556 A1    Aug. 3, 2017

(30) Foreign Application Priority Data

Sep. 30, 2014 (EP) ..................................... 14187175
Jan. 23, 2015 (EP) ..................................... 15152329

(51) Int. Cl.
*B01L 3/00*     (2006.01)
*B01L 7/00*     (2006.01)
(Continued)

(52) U.S. Cl.
CPC .......... *G01N 33/48707* (2013.01); *B01L 7/00* (2013.01); *G01N 27/126* (2013.01);
(Continued)

(58) Field of Classification Search
CPC .. C12Q 1/001; C12Q 1/6834; G01N 27/3276; G01N 33/4836; G01N 33/0031;
(Continued)

(56) References Cited

U.S. PATENT DOCUMENTS

2002/0122747 A1    9/2002  Zhao et al.
2002/0142477 A1*  10/2002  Lewis ................ G01N 33/0031
                                                            436/151
(Continued)

OTHER PUBLICATIONS

"Microfluidic gas sensor with integrated pumping system", Sensors and Actuators B: Chemical, vol. 170, Jan. 21, 2011 (Jan. 21, 2011), pp. 45-50, XP055159742, ISSN: 0925-4005.
(Continued)

*Primary Examiner* — Jennifer Wecker
(74) *Attorney, Agent, or Firm* — Muncy, Geissler, Olds & Lowe, P.C.

(57) ABSTRACT

A detection device for detecting a marker in a liquid, preferably a fuel, comprising:
a reaction chamber 5, provided with a de-dopable conductive polymer 6 building a path between two conductive pads 10 connected to a resistivity measurement device, wherein the de-dopable conductive polymer 6 is able to be de-doped by a chemical reaction with the marker, changing its resistivity.

24 Claims, 9 Drawing Sheets

(51) Int. Cl.
  *G01N 27/12* (2006.01)
  *G01N 33/487* (2006.01)
  *G01N 33/28* (2006.01)
  *C12Q 1/68* (2018.01)
  *G01N 27/447* (2006.01)
  *G01N 27/327* (2006.01)
  *C12Q 1/6834* (2018.01)
  *C12Q 1/00* (2006.01)
  *G01N 33/483* (2006.01)

(52) U.S. Cl.
  CPC .... *G01N 33/2882* (2013.01); *B01L 3/502707* (2013.01); *B01L 2200/12* (2013.01); *B01L 2300/0645* (2013.01); *B01L 2300/0816* (2013.01); *B01L 2300/0887* (2013.01); *B01L 2300/1827* (2013.01); *B01L 2400/0415* (2013.01); *B01L 2400/0421* (2013.01); *C12Q 1/001* (2013.01); *C12Q 1/6834* (2013.01); *G01N 27/3276* (2013.01); *G01N 27/4473* (2013.01); *G01N 27/44791* (2013.01); *G01N 33/4836* (2013.01)

(58) Field of Classification Search
  CPC ............. G01N 27/126; G01N 33/0047; G01N 27/44704; G01N 27/4473; G01N 27/44791; B01L 2200/12; B01L 2300/0645; B01L 2300/0816; B01L 2300/0887; B01L 2300/1827; B01L 2400/0415; B01L 2400/0421; B01L 3/502707; B01L 7/00
  See application file for complete search history.

(56) References Cited

U.S. PATENT DOCUMENTS

2004/0040841 A1\* 3/2004 Gonzalez-Martin ........................ G01N 27/126 204/406
2016/0051982 A1\* 2/2016 Rawle ................ G01N 21/0332 435/6.12

OTHER PUBLICATIONS

International Search Report and Written Opinion issued with respect to application No. PCT/EP2015/072108.
Eurasia office action in counterpart Eurasian Application No. 201690337/31 dated Nov. 14, 2016 (and English language translation).
Eurasian office action in counterpart Eurasian Application No. 201690337/31 dated Jan. 23, 2017 (and English language translation).

\* cited by examiner

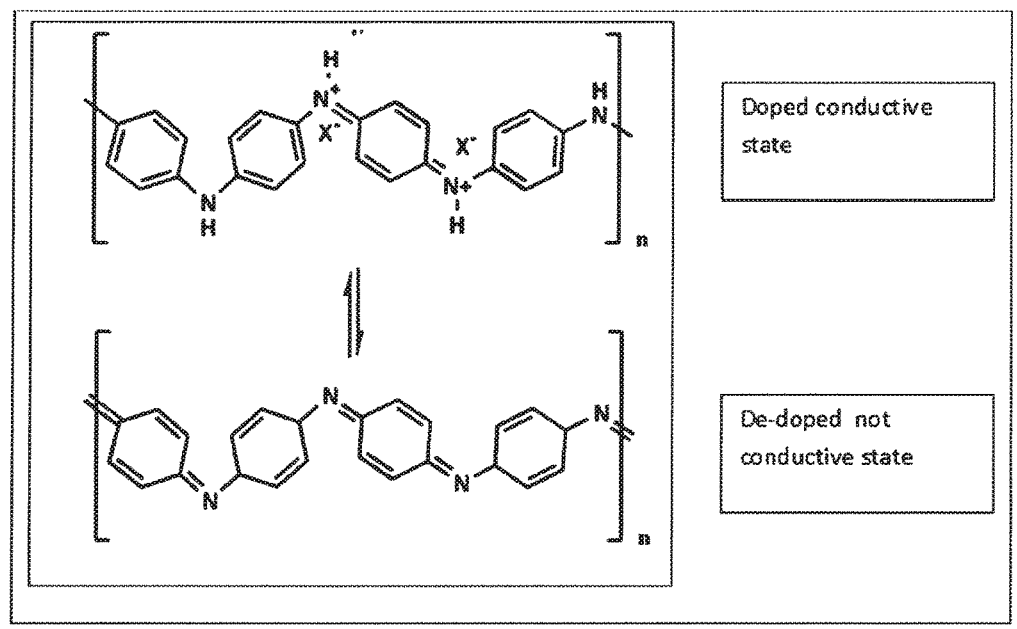
Figure 9
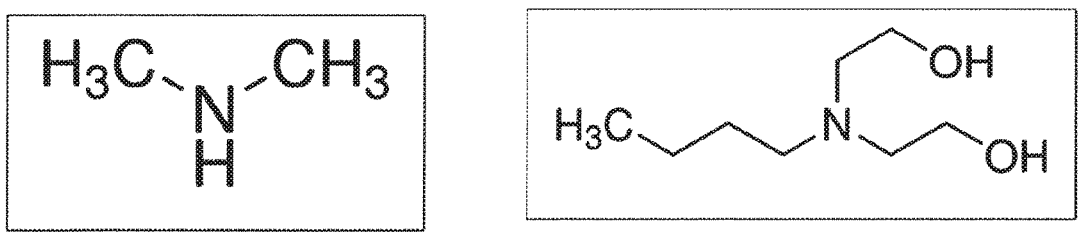
Figure 10
Figure 11
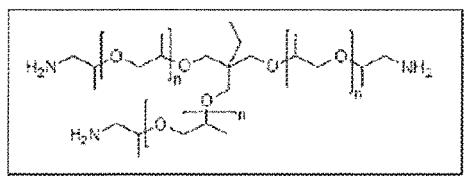
Figure 12
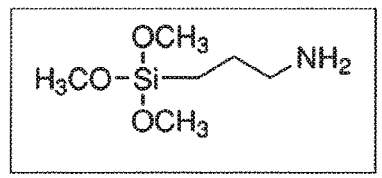
Figure 13

DETECTION DEVICE TO IDENTIFY MARKERS DISSOLVED IN A LIQUID BY MEANS OF A MEASUREMENT OF RESISTIVITY VARIATION, DETECTION METHOD AND USE OF MARKER AND DETECTION DEVICE

TECHNICAL FIELD

The technical field is the detection of reactive molecules in a liquid environment. These reactive molecules can act as marker for the liquid, serving as authentication means for verifying the authenticity and/or origin of the liquid.

BACKGROUND OF THE INVENTION

Conductive polymers are presently known materials. Also, conductive polymers are partly commercially available. They are currently considered as material for integrated circuits, light emitting devices, antistatic materials, displays and batteries.

However, conductive polymers are generally difficult to process and have poor stability, which greatly limits their applicability in various applications. For an application to detect markers in a liquid, the currently available conductive polymers typically exhibit stability problems, as the original physical shape undergoes variations as a consequence of the contact with liquids, particularly at increasing temperature, and in organic solvents. This shape variation causes a variation of the electrical properties and a degradation of the polymer during storage.

On the other hand, it is often desired to verify the origin and authenticity of liquids of various kinds, such as fuels (e.g. diesel, kerosene, gasoline etc.) in order to be able to identify forged or non-genuine products. For this purpose, a marking substance (marker) is often added to the liquid, such as a specific dye. The addition of a marker is also employed in order to distinguish between liquids that are chemically identical or very similar, but which are regulated differently. One example is the addition of a certain dye into heavily taxed diesel fuel in Germany, while the chemically very similar or identical heating oil is taxed at a lower rate and is not marked with a specific dye. The identity of a liquid in a car tank can then be assessed by analyzing the liquid as to presence of the specific marker dye.

The authenticity of the liquid is then assessed by means of a detector, e.g. a colour detector or spectral analysis in case of a certain dye. Yet, often bulky and expensive equipment is needed in order to detect the marker. Further, the marker often needs to be present in significant quantities in order to allow a reliable detection. In another aspect, the marking can be easily counterfeited if commercially available substances (e.g. dyes) are used, as only the properties of the marker (but not its interaction with a detection device) are assessed.

OBJECTS OF THE INVENTION

One object of the present invention is to provide a cheap and portable solution for detecting the presence of a marker at low concentration in a liquid, which is preferably a fuel. The proposed markers should exhibit good solubility in the liquid. The marker should further be difficult to extract and separate. Further, the marker should be relatively easy to identify by means of special and authorized equipment, while it should be relatively difficult to identify and detect without special or authorized equipment. The solution should be able to detect the presence of a suitable marker inside the liquid, preferably a fuel, in little time, preferably in the course of a few minutes, or, more preferably, in the course of less than a minute.

The present invention aims further at providing a method for authenticating the origin and/or authenticity of a liquid, preferably a fuel, that is easy to implement and which provides a security level that is higher than those of conventional authentication methods.

The present invention further aims at providing a new use of polymer having variable conductivity which does not, or to a smaller degree, suffer from the drawbacks of conductive polymers above.

SUMMARY OF THE INVENTION

The mentioned problems and objects are solved by the subject-matter of the independent claims. Further preferred embodiments are defined in the dependent claims and are also described in the following specification.

The present invention therefore provides the following and further following preferred embodiments.
1. A detection device for detecting a marker in a liquid, preferably a fuel, comprising:
    a reaction chamber, provided with a polymer formulation with variable conductivity building a path between two conductive pads connected to a resistivity measurement device,
    wherein the conductive polymer formulation is able to react with a marker to thereby change its resistivity.
2. The detection device according to item 1, wherein the polymer formulation with variable conductivity comprises a polymer with variable conductivity and an insulating polymer, wherein the amount of polymer with variable conductivity is 10% by weight or higher and less than 65% by weight, relative to the total weight of polymer with variable conductivity and insulating polymer.
3. The detection device according to item 1 or item 2, wherein the polymer formulation is obtainable by photo-curing a photocurable polymerizable composition comprising a conductive polymer, precursor compounds capable of forming an insulating polymer and a photoinitiator.
4. The detection device according to any one of items 1, 2 and 3, wherein the insulating polymer comprises a polar group in the polymer main chain and/or side chain, which is preferably selected from selected from ether groups, ester groups, carbonyl groups, secondary and tertiary amine groups, amido groups, amide groups, amino groups, hydroxyl groups, —S(O)— and —S(O)$_2$—.
5. The detection device according to any of the preceding items 1 to 4, further comprising:
    a heater element suitable to heat and to evaporate the marker dissolved in the liquid, and optionally an element capable of performing a distillation operation.
6. The detection device according to any of the preceding items 1 to 4, further comprising a housing for enclosing the reaction chamber and a housing cover comprising a printed circuit board, wherein said conducting pads are arranged on said printed circuit board facing the reaction chamber.
7. The detection device according to item 6, wherein said housing comprises a heat conducting part on a side opposing said conductive pads, wherein a volume is arranged between said heat conducting part and said conductive pads.

8. The detection device according to any of the preceding items, wherein the reaction chamber is coated with the polymer formulation with variable conductivity.
9. The detection device according to any of the preceding items, wherein a marker diluted in the liquid at a concentration smaller than 150 ppm generates on the polymer with variable conductivity a resistivity change greater than 30%, preferably greater than 50%, more preferably greater than 100%, relative to the resistivity prior to contact with the marker.
10. The detection device according to any one of items 3 to 9, wherein the photocurable polymerizable composition comprises:
   a) 15 to 50% wt of a polymer with variable conductivity, preferably polyaniline, or monomers or oligomers able to generate a polymer with variable conductivity as a consequence of a polymerization reaction;
   b) 20 to 60% wt of a (meth)acrylate monomeric or oligomeric species able to generate, after a polymerization reaction, an insulating polymer;
   c) 1 to 10% wt, of a radical photoinitiator;
   d) 0 to 60% wt of an organic solvent, preferably xylene; based on the total weight of the photocurable composition.
11. The detection device according to any one of items 1 to 10, wherein the weight ratio insulating polymer/variable conductive polymer in the polymer formulation with variable conductivity, respectively in the polymerizable composition used to produce the polymer formulation with variable conductivity, is between 0.5 and 2.5.
12. The detection device according to any one of items 1 to 11, wherein the polymer formulation with variable conductivity changes its resistivity upon contact with a marker capable of abstracting a proton therefrom.
13. A system comprising:
   A. A detection device according to any of the preceding items;
   B. A fuel as said liquid;
   C. A marker dissolved in the fuel with a concentration<150 ppm, which is preferably an amine.
14. A method for manufacturing a detection device according to any one of items 1 to 12 comprising the steps of:
   depositing a polymerizable composition comprising a) a polymer with variable conductivity, b) precursor compounds capable of forming an insulating polymer, and c) a photoinitiator on the walls and/or on the floor of the reaction chamber and/or on the conductive pads;
   irradiating the polymerizable composition, preferably with UV radiation.
15. The method according to item 14, wherein the weight ratio insulating polymer/polymer with variable conductivity in the polymerizable composition used to produce the polymer formulation with variable conductivity is between 0.5 and 2.5.
16. A method for detecting a marker in a liquid, comprising the steps of:
   optionally concentrating and/or separating the marker from the liquid;
   introducing the marked liquid, a concentrated material obtained therefrom or the separated marker, into a reaction chamber of a detecting device, the reaction chamber containing the polymer formulation with variable conductivity such as to build a path between two conductive pads connected to a resistivity measurement device;
   letting the marker react in the reaction chamber with the polymer formulation comprising a polymer with variable conductivity; and
   measuring the resistivity change of the polymer formulation comprising the polymer with variable conductivity.
17. The method according to item 16, wherein the step of concentrating and/or separating the marker from the liquid is conducted and includes the evaporation of the marker from the liquid.
18. The method according to any one of items 16 and 17, wherein a device according to any one of items 1 to 10 is used.
19. The method according to any one of items 16 to 18, wherein the liquid is a fuel, the marker is a diluted marker, preferably an amine, dissolved in said fuel, and the insulating polymer is a polymer having a polar group.
20. Use of a polymer with variable conductivity for verifying the authenticity or genuineness of a liquid comprising a marker, the use comprising a measurement of the resistivity of the polymer with variable conductivity, or of a polymer formulation comprising it, before and after contact with the liquid.

DETAILED TECHNICAL DESCRIPTION

Figure 1:
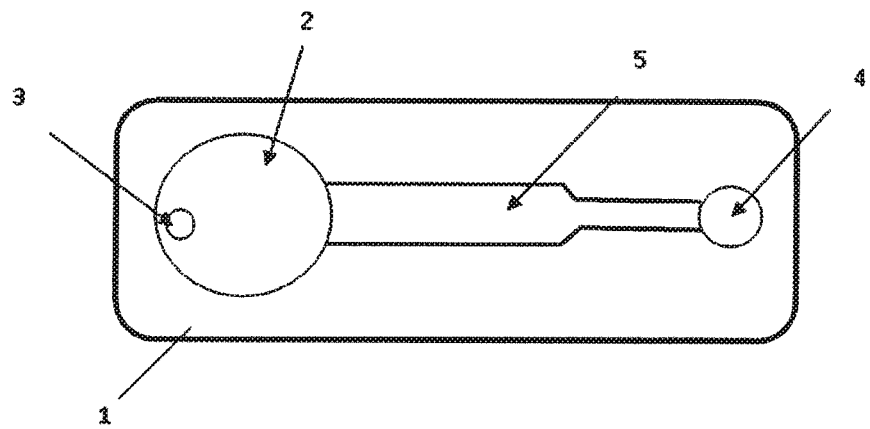
FIG. 1. Microhydraulic 1 of the inventive conductivity detecting device
FIG. 2. Microhydraulic 2 of the inventive conductivity detecting device
FIG. 3. PCB (printed circuit board) containing electrical tracks and the inventive polymer with variable conductivity
FIG. 4. Conductimetric vapor detecting device (top layer)
FIG. 5. Conductimetric vapor detecting device (bottom layer)
FIG. 6. Conductimetric vapor detecting device
FIG. 7. Electrical resistance variation of polymer C4 after contacting fuel with and without marker
FIG. 8. Relative percentage electrical resistance variation of polymer C4 after contacting fuel with and without marker
FIG. 9. Polyaniline molecular structure in doped and de-doped state
FIG. 10. Dimethylamine
FIG. 11. N-butyldiethanolamine
FIG. 12. Jeffamine T-403
FIG. 13. Silquest A1100
FIG. 14. Diethylenetriamine
FIG. 15. Dimethylethanolamine
FIG. 16. 2,4,6-Tris(dimethylaminoethyl)phenol
FIG. 17. Triethylamine
FIG. 18. Tetrabutylammonium dihydrogenphosphate monobasic
FIG. 19. Xylene
FIG. 20. PEG monoacrylate (MW360)
FIG. 21. Polyaniline (Emeraldine salt)
FIG. 22. Trimethylolpropane ethoxylated triacrylate (MW428) and trimethylolpropane ethoxylated triacrylate (14EO/3OH)
FIG. 23. Esacure TPO
FIG. 24. Glycerol 1,3-diglycerolate diacrylate
FIG. 25. A schematic view of test equipment according to an embodiment of the present invention
FIG. 26A. A schematic view of said test equipment during operation according to another embodiment of the present invention FIG. 26B. A schematic view of said test equipment during operation according to another embodiment of the present invention FIG. 27. Resistance variations obtained with different concentrations of marker (triethylamine) in diesel fuel.

The present invention exploits a resistivity change of a polymer formulation with variable conductivity that is observed when the polymer formulation is brought into contact with a liquid containing a marker substance. Herein, the marker is capable of undergoing a chemical reaction and/or a doping/de-doping process with the polymer with variable conductivity present in the polymer formulation, to thereby cause a change in the conductivity or resistivity of the polymer formulation.

Definitions

The following terms will be used in the following description:

The term "conductive polymer" is used to denote a polymer that is electrically conductive at ambient temperature (20° C.), also known as intrinsically conductive polymers (ICPs).

The term "polymer with variable conductivity" is used to denote a polymer able to vary its conductivity at a certain temperature in function of its contact to molecules able to stabilize or neutralize a positive charge or negative charge on the polymer.

Herein, the term "electrically conductive" is used to denote a material having a conductivity of $10^{-2}$ S/cm or greater, preferably $10^0$ S/cm or greater, more preferably $10^2$ S/cm or greater.

The term "insulating" is used to denote a material having a conductivity of less than $10^{-2}$ S/cm, preferably a conductivity of $10^4$ or less, more preferably $10^{-6}$ or less. The term "inert" is used to denote a material not able to change from an insulating state to a conductive state.

The conductivity of a polymeric material can be determined by methods known to the skilled person. For instance, the method defined in ISO 3915:1981 (last reviewed 2009) can be used.

The term "polymer formulation" is used to denote a composition comprising an insulating inert polymer and a polymer with variable conductivity.

The terms "$K_b$ value" and "$K_a$ value" are used to denote the basic and acid dissociation constant of a material, measured at 20° C. and for an aqueous solution.

The term "fuel" is used to denote liquid compositions that is or can be used as chemical energy source in order to promote engine motion, such as in cars, airplanes or ships. The term also covers liquid compositions used for heating purposes. Examples of fuels include diesel, gasoline, kerosene, ethanol, liquefied petroleum gas (LPG), and other fuel oils such as naptha.

The term "comprising" is open-ended and allows for the presence of further components that are not explicitly recited. Yet, the term "comprising" also encompasses the more restrictive meanings "consisting of" and "consisting essentially of", so that further components other than those explicitly recited may be completely or substantially absent.

The term "one or more" is used to denote that at least one of the following materials or elements is present. Typically, the term is used to denote the presence of one, two, three, four, five or six of the respective materials or elements, more preferably one, two or three, further preferably one or two.

In the following specification, all physical properties refer to those measured at standard conditions (20° C., 1 atm pressure), unless it is indicated otherwise The elements and materials used in the present invention will now be described.

Device

According to an embodiment of the invention, a device is proposed that is able to detect low concentrations of different markers diluted in a liquid, preferably a fuel, and preferably at low concentrations (e.g. at a concentration≤100 ppm). The device contains a strip or layer of polymeric material with a variable conductivity, preferably composed of a polymer formulation comprising an insulating polymer and a polymer with variable conductivity in a (doped) conductive state or in a (de-doped) insulating state. The polymer with variable conductivity will undergo a variation of its conductive properties when it is contacted with one or more markers, or liquids containing one or more markers, able to de-dope or dope it. This change in resistivity is used directly or indirectly as means for verifying the authenticity of the liquid.

As a consequence of the contact with the marker, the device will show a variation of the conductivity of the strip or layer of polymeric material, which can be determined as follows: The ends of the strip or layer can be contacted by suitable electrodes and the resistance before and after the de-doping or doping reaction can be measured. By recording the resistance values only, or by recording the resistance values vs. time, it will be possible detect the marker with great reliability and in small concentrations. If the resistance change over time is recorded, it is possible to plot a curve that will depend on the kinetics of the reaction of the marker and the polymeric material. As such, also the measurement temperature may influence the magnitude and/or speed of the resistance variation, and may thus also be considered for authentication purposes. Within certain boundaries, the present invention can thus distinguish between different markers, and can distinguish between different concentrations of the same marker.

In order to have a portable device, such as a lab on chip (LOC or MEMS or chip) of minimal size able to detect a marker solubilized in a liquid, e.g. a fuel, in concentration equal to or lower than 1,000 ppm or even 100 ppm, a device has been developed containing a formulation comprising an insulating polymer and a polymer able to vary its conductivity, so that the formulation can show an intrinsic conductivity variation that is detectable by means of a simple resistivity tester. Such a device can then be used on-site, without the need for sending the liquid for analysis to a laboratory, and is further easy to handle even by untrained users.

The device preferably comprises three communicating regions:
- the injection chamber, where the marked liquid is introduced;
- the doping/de-doping or reaction chamber with one or more sides, preferably including the bottom (and optionally the walls) being coated by the polymer formulation with variable conductivity;
- a third chamber, connected to the reaction chamber, used for venting/flushing the device.

A suitable marker present in the liquid (e.g. the fuel) is able to promote a reaction of the polymer with variable conductivity present in the polymeric formulation. In case of de-doping reaction, this will bring the polymer with variable conductivity toward an insulating or significantly less conductive state, and this will cause a conductivity decrease with preferably specific reaction kinetics. While the observed resistivity change, or the resistivity change over time, will thus mainly depend on the kind and amount of marker as well as the type and amount of polymer with variable conductivity in the polymer formulation, it will also depend on other factors, such as the penetration of the liquid fuel into the polymer formulation, the contact time with the liquid and the geometry of the reaction chamber.

Similarly the doping reaction will promote a conductivity increase of the polymer with variable conductivity.

Preferably, the device is able to detect the presence of one or even more than one reactive markers in a liquid. Particularly, several classes of markers could be detectable (inorganic bases or acids, organic bases such as amines, alcoholates, thiolates or carboxylates, organic acids such as carboxylic acids, such as acetic acid or propionic acid, organometallic bases or acids, reducing agents on one side; acids and oxidizing agents on the other side). Each of these molecules ideally could be recognized on the basis of its specific kinetic of the doping or de-doping reaction.

In one preferred embodiment, the device contains a section equipped with heater element for heating the liquid to be tested up to a temperature where a significant fraction of the one or more markers in the liquid evaporates. The temperature to which the liquid is heated in the section containing the heater element depends on the kind of liquid tested and the kind of marker(s) employed, but is typically in the range of 50-250° C., more preferably 60 to 200° C., even more preferably 80 to 150° C.

All or the majority of marker present in the liquid will then evaporate. This allows bringing the more concentrated marker(s) into contact with the polymer formulation with variable resistivity, which facilitates the doping or de-doping reaction and thus the change in resistivity that is used as an authentication means.

The evaporated marker(s) can be supplied to the polymer formulation with variable resistivity as vapor after the evaporation, but can also be condensed by a condensing means before being brought into contact with the polymer formulation with variable resistivity. In the latter case, the condensing means may be simply a surface of the device, but also a cooled surface may be provided on which the marker(s) condense. Then, the condensed marker(s) are transferred to the polymer formulation with variable resistivity. It is also possible to employ a distillation column-type arrangement as a condensing means, such as having a number of theoretical plates of 1 or greater, 2 or greater, 3 or greater, or 10 or greater.

The concentration of the marker in the material to be supplied to the polymer after evaporation and optionally condensation and/or distillation is greater than in the liquid to be tested. Preferably, it is 0.1% by mass or greater, more preferably 1% by mass or greater, and can be as high as 100% by mass or less, 80% by mass or less, or 50% by mass or less. The degree of enrichment of the marker(s) depends on the kind(s) of markers used and the effectivity of the evaporation and optional distillation operation.

By providing a heater element for evaporating the marker(s) and optionally a distillation column-type arrangement, the concentration of the marker(s) is increased. This increases the sensitivity of the device. Further, the higher concentration of the marker(s) decreases the contact between the polymer formulation and the bulk liquid to be tested, which improves the signal-to-noise ratio.

In the embodiment wherein a distillation column-type arrangement is provided, several marker(s) present in the liquid can be separated and measured independently of one another. This allows for a "masking" of the "true" marker. For instance, if a small amount of trimethyl amine is used as marker, yet this is present in the liquid simultaneously with a larger amount of triethyl amine, a counterfeiter may be able to detect only the trimethylamine, or assume that only this species is indicative and will be tested as a marker for the authenticity of liquid. Measuring the amount and/or presence of trimethyl amine in this example allows for a secure identification of a genuine liquid.

Besides a heater element and optionally a distillation-column type arrangement for at least partially separating the marker(s) from the liquid to be tested, naturally also other separation technologies can be contemplated, such as a use of adsorbents for the marker(s) followed by desorption, HPLC technologies, etc. However, these technologies typically require the supply of further components to the device, such as adsorbents, solvents for HPLC et cetera, which are not required for a separation by a heater element and optionally a distillation column-type arrangement. This increases costs, and such materials may also not be available at the testing site. Hence, it is an advantage of the device according of the present invention that no materials other than the test liquid are consumed and/or need to be supplied for performing the test.

Figure 24:
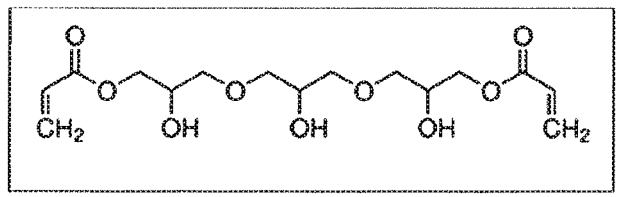
Figure 25:
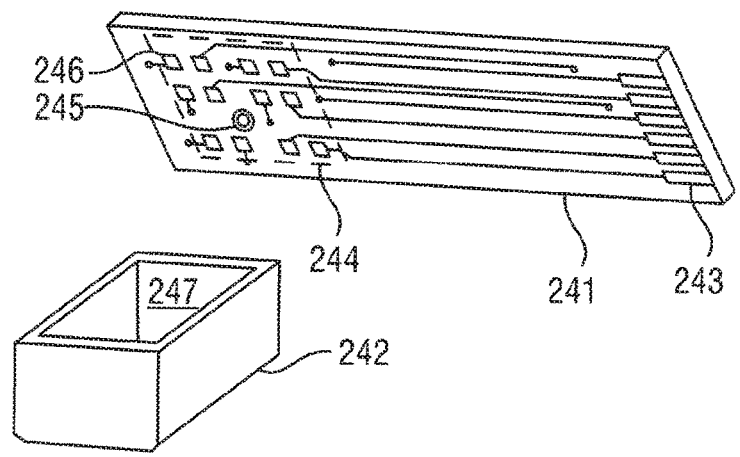

FIG. 24 shows a schematic view of test equipment according to a device embodiment of the present invention. Specifically, such test equipment comprises a device with a printed circuit board (PCB) 241 and a housing 242. Note that FIG. 25 shows the device in its disassembled state. Normally, i.e. for and during operation of the device, the housing 242 is affixed along the area 244 of one side of the PCB 241. The PCB 241 comprises conductive lines so as to connect test pads 246 with contact pads 243. The latter pads 243 allow for an electrical connection toward further test equipment specifically configured to examine the electrical characteristics between respective test pads 246.

The housing 242 when affixed to the PCB 241 forms an enclosed volume 247 as some kind of reaction chamber for holding test substances, such as a test liquid under consideration and examination. In particular, the volume 247 is accessible through a sealed orifice 245 either in the PCB 241 (as shown) or elsewhere in the housing 242. By means of said orifice 245 the test substance (liquid) can be introduced into the volume 247. The orifice 245 may feature a rubber or in general elastic or membrane seal (e.g. rubber, silicone, etc.) that can be penetrated and punctured by, for example, a cannula of a syringe. Further orifices may be provided for allowing venting and/or flushing the enclosed volume 247.

In general, the volume 247 includes the reaction chamber for allowing the implementations for resistivity tests according to the embodiments of the present invention. Specifically, a polymer formulation with variable conductivity may build a path between two of the pads 246 connected to a resistivity measurement device via the conductive lines and the connection pads 243. As shown in FIG. 25, a set of pad pairs is arranged so as to be accessible inside the volume 247 and the reaction chamber. In this way, several identical or different polymer formulations may be employed for testing one formulation more than one time or to test different formulations. Such a way forward may advantageously increase flexibility and/or reliability. However, the embodiments of the present invention may require only one path of a polymer formulation between a single pair of pads.

Figure 26A:
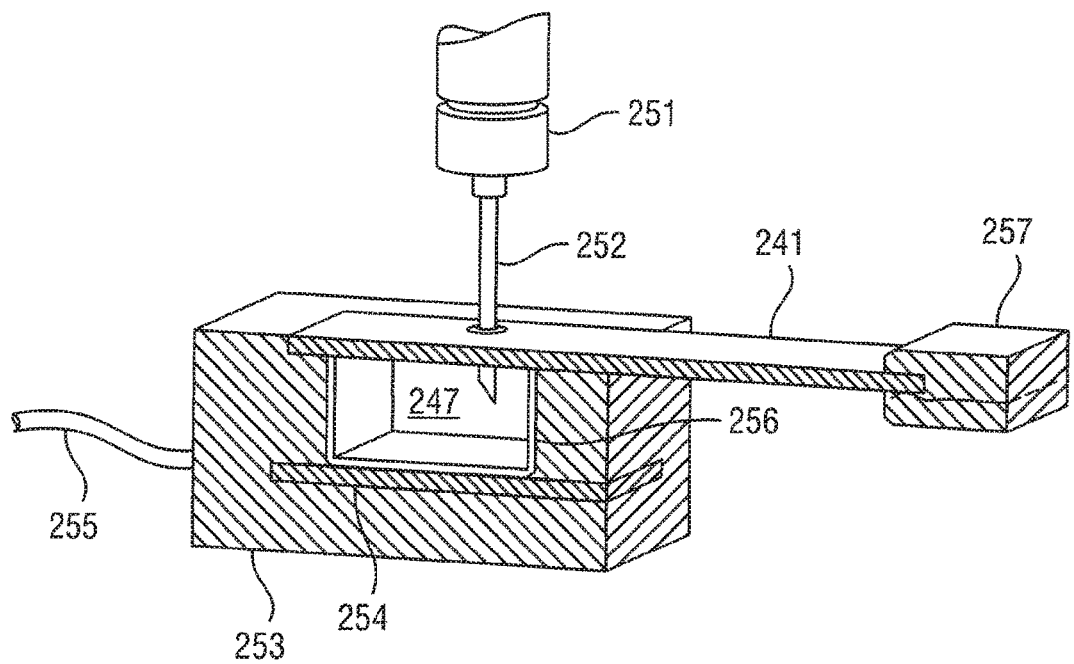

FIG. 26A shows a schematic view of said test equipment during operation according to another embodiment of the present invention. The test equipment as shown includes a base 253 which is shown in a cross-sectional fashion (see hatched areas). The base 253 provides an opening (pocket) 256 that fits the housing 242 of the test device as described in conjunction with FIG. 25. Further means (as such not shown) for holding securely the device on and in base 253 may be provided in the form of brackets and the like. As shown, the device is inserted in the base 253 so that the reaction chamber 247 can be filled, at least in part, with a test substance/liquid by means of a syringe 251 and a cannula 252 which can penetrate the orifice 245. Other sample equipment may be employed to bring a sufficient amount of test fluid into volume 247. Further, the device is inserted in the base 253 so that the connectors of the PCB 241 can be connected to some sort of plug contact 257 so as to connect ultimately the pads 246 to a resistivity measurement and examination circuitry.

As further shown in FIG. 26A, the base 256 comprises a heating element 254 which is arranged to at least heat a part of the housing 242 when inserted or in sufficient thermal contact thereto. A set 255 of electrical cables may lead power to the heating element 254 and possibly also connect to a temperature sensor inside the base so as to allow for a feed-back control of the heating of the housing 242. As a consequence, the chamber 247 and some of its contents is also heated which allows the controlled formation of conductivity within the path of the polymer formulation. In general, heating may promote formation of conductivity in an accelerated and/or more reproducible or reliable fashion. As far as the housing 242 is concerned, a heat conducting part may be arranged in the housing on the side where it contacts the heating element 254. This may be achieved by a aluminum, copper, or the like, plate embedded in a housing manufactured, for the remainder, from plastics. However, also the entire housing may be manufactured from a material with good heat conducting properties, such as aluminum, copper, brass, etc., where the latter two can be advantageously soldered to the PCB 241.

In general, the heating element 254 may be employed to concentrate and/or separate a marker from the substance or liquid in the chamber 247. Preferably, this concentrating may include evaporation of the marker from a liquid as shown schematically in FIG. 26B as test equipment during operation according to another embodiment of the present invention. More specifically, the heating element 254 is employed to heat up a test liquid 258 inserted via syringe 251. The up-side-down configuration of having the liquid test substance at the bottom of chamber 247 and housing 242, and having the test pads and the polymer formulation atop the test liquid advantageously allows for reliable precipitation of a marker 259 evaporated from the liquid by means of suitable heating. Such heating may be conducted in a more or less controlled fashion so as to attain a temperature high enough to achieve marker evaporation but sufficiently low for not altering the resistivity characteristics of the employed polymer formulation and to keep the setup as a whole stable. For example, it should be ensured that no liquid escapes the chamber 247, so the vapor pressure at a given maximum temperature may be considered by the associated control arrangement.

Figure 26B:
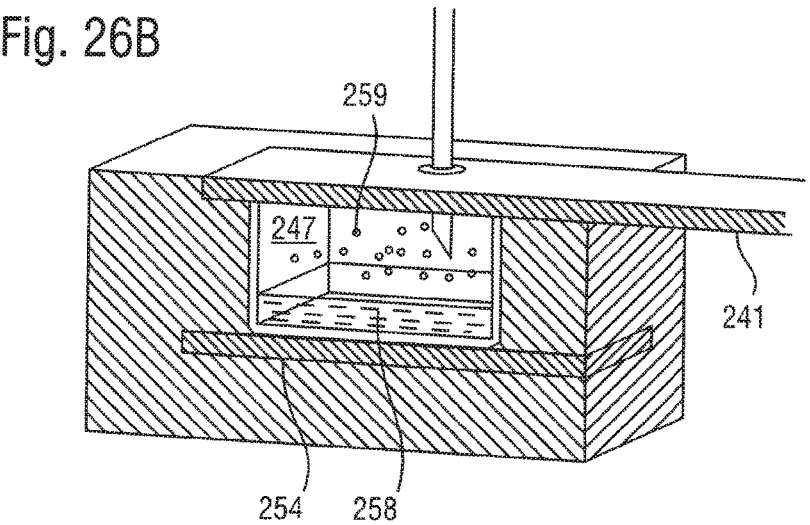

In general, the test equipment as shown and described in conjunction with FIGS. 25, 26A, and 26B, can be implemented as a re-usable or in an at least disposable configuration. In the latter, the device with the PCB 241 and the housing 242 is configured to receive a test liquid only for one test. In this way, the housing 242 can be permanently affixed to PCB 241 which will reduce manufacturing cost. Likewise, the orifice 245 may be in the form of a sealing membrane that protects the polymer formulation in the period before use and ruptures when a cannula 252 is inserted. The device with the PCB 241 and the housing 242 is then configured as a disposable device that is to be disposed of after use. On the contrary the base 253 and the associated elements may be configured in a multi-use setup so as to allow testing with many devices 241/242.

Liquid

The liquid tested for its authenticity and/or genuineness in the present invention is not particularly limited, but is preferably a fuel as defined above. In one embodiment, the liquid is hydrocarbon-based, with preferably 90% by mass or more of the liquid consisting of one or more hydrocarbons (i.e. compounds consisting of hydrogen and carbon only). In another embodiment, the liquid is a material of high value, such as spirits (e.g. Whiskey) or perfumes.

Marker

The marker is a substance that is present in the liquid (e.g. the fuel) to be tested for its authenticity and/or origin. It is typically dissolved in the liquid. As the marker is indicative for the authenticity and/or origin of a liquid, the marker is typically a compound that is added to the liquid on purpose. Put differently, the marker is typically not a compound that is naturally occurring in the liquid.

The marker is not particularly limited, and the choice of the marker depends on the chemical reaction that is to be caused. As one typical example, the chemical reaction is a de-doping of the conductive polymer. Herein, the term "de-doping" denotes a reaction resulting in the neutralization of positive charges present on the conductive polymer. The conductive polymer changes its resistivity in response to this de-doping, and typically becomes less conductive, more preferably insulating.

The term "doping" denotes the introduction of a positive or a negative charge onto the insulating polymer. The insulating polymer changes its resistivity in response to doping and typically becomes more conductive.

In case the de-doping chemical reaction to be caused is a proton abstraction (more in general a nucleophilic interaction), the marker is a chemical species capable of accepting a proton (Bronsted base) or acting as a nucleophile towards the positive sites of the polymer with variable conductivity. In view of their good solubility in organic liquids, such as fuels, the preferred markers are organic bases, like amines, alcoholates, thiolates, carboxylates and organometallic compounds (e.g. alkyl metals, such as butyl lithium). Among these, amines are more preferred as a consequence of their good stability and low reactivity with organic solvents in which they could be diluted, with aliphatic amines being particularly preferred.

The amine marker can be a primary, secondary or tertiary amine or the formula $NR^1R^2R^3$. Herein, $R^1$, $R^2$, and $R^3$ are either hydrogen or an organic group. The organic group represented by $R^1$, $R^2$, and/or $R^3$ preferably has 1 to 20 carbon atoms, more preferable 2 to 10 carbon atoms, and can be an aliphatic or aromatic group. The group can further contain 0, 1, 2, 3, 4 or 5 heteroatoms selected from oxygen, nitrogen and sulfur. Further preferably, $R^1$, $R^2$, and $R^3$ represent either hydrogen or an organic group containing only carbon and hydrogen atoms, and optionally one or two oxygen atoms. More preferably, one or two of $R^1$, $R^2$, and $R^3$ represent a hydrogen atom, and the remaining one or two of $R^1$, $R^2$, and $R^3$ represents an alkyl group having 1 to 12, preferably 1 to 6 carbon atoms, which may each be substituted by one or two hydroxyl groups. Examples of amines of $NR^1R^2R^3$ include methylamine, dimethylamine, trimethylamine, ethyl dim ethyl amine, methyldiethylamine, diethylamine, triethylamine, N,N-diisopropylmethyl amine, propylbutylamine, aniline, 2,4,6-tris(dimethylaminoethyl)phenol and 4-methylaniline.

The amine marker can also be a cyclic amine wherein a basic nitrogen atom is part of a ring system. The ring system can be aromatic or aliphatic and may contain one, two, three or four basic nitrogen atoms, preferably one or two basic nitrogen atoms. Examples of cyclic amines include pyridine, pyrrolidine, pyrimidine, pyrazole, purine, piperidine, 2,2,6,6-tetramethylpiperidine, 4-dimethylaminopyridine (DMAP), and 4-dimethylaminophenol.

Further examples of cyclic and non-cyclic amines are shown in FIGS. 10 to 18 and are listed in tables 1 to 3. It is pointed out that the amines defined above may be non-substituted, but can optionally be substituted with common substituents of organic compounds, such as a hydroxyl group, an alkoxy group, an oxo group, a cyano group, a nitro group, etc. Preferably, the amine has no, one or two substituents, such as for instance in methyldiethanolamine having two hydroxyl substituents. An aminoalcohol is thus a preferred embodiment of the marker. Of course, an amine marker may comprise more than one basic nitrogen, e.g. one, two, three or four basic nitrogen atoms. Herein, the term "basic" denotes a $K_b$ value of greater than $10^{-10}$, preferably greater than $10^{-4}$.

The marker can also be an alcoholate or thiolate. Preferred alcoholates include alkali metals salts of primary, secondary and tertiary monohydric alcohols, such as potassium tert-butoxide. Preferred thiolates include alkali metal salts of thiols, such as sodium thiophenolate.

If the change in resistivity of the polymer with variable conductivity, respectively the polymer formulation comprising it, is to be caused by nucleophilic interaction toward the positive charges of the polymer in its conductive form, the marker needs to be a Lewis base, a Broensted base or a nucleophilic compound. Further, preferably the method and device of the present application are able to detect even minute amounts of the marker. In order to allow the detection of minute amounts of marker in a fuel, the equilibrium between the ionized form of the marker (after nucleophilic interaction toward the iminic nitrogen of polyaniline conductive polymer) and the non-ionized form (prior to a nucleophilic interaction toward the iminic nitrogen of polyaniline conductive polymer) as present in the liquid to be tested is preferably greatly on the side of the reacted form. When the marker acts as a base the $K_b$ value of the marker is preferably $10^{-10}$ or greater, more preferably $10^{-8}$ or greater or $10^{-6}$ or greater, further preferably $10^{-4}$ or $10^{-2}$ or greater. In some further preferred embodiments, the $K_b$ value of the marker may be as high as 1 or even greater. These Kb values apply to all markers, in particular the amines, but also the thiols and alcoholates.

In case the doping chemical reaction to be caused is a proton donation (more in general an electrophilic interaction), the marker is a chemical species capable of releasing a proton (Broensted acid) or acting as an electrophile towards the reactive nitrogen atoms of the polymer with variable conductivity. In view of their good solubility in organic liquids, such as fuels, useful markers are organic acids, Lewis acids (or their complexes), organometallic compounds, molecules able to generate (by UV or thermal decomposition) acids.

In another aspect, the marker preferably is a compound with low molecular weight in order to allow permeation and diffusion into the polymer formulation. The marker therefore preferably has a molecular weight of less than 2000, further preferably less than 500, and most preferably less than 350 g/mol.

The amount of the marker in the liquid to be tested that is necessary in order to cause a detectable change in resistivity of the polymer formulation depends on $K_b$ and $K_a$ value of the marker, the $K_b$ and $K_a$ value of the polymer with variable conductivity and the ease of diffusion of the marker into the polymer with variable conductivity in order to have interaction. While therefore the amount of marker can be varied over a great range, the concentration of the marker in the liquid (e.g. fuel) to be tested is typically 5,000 ppm (by weight) or less, preferably 1,000 ppm (by weight) or less, more preferably 500 ppm (by weight) or less, and even more preferably 100 ppm (by weight) or less. A lower amount of marker is also preferably in order to minimize the risk of interference of the marker with the properties of the liquid in its later use, e.g. in order to avoid corrosion inside a combustion engine if the liquid is fuel.

In embodiments of the present invention wherein the marker is evaporated prior to contact with the polymer formulation with variable conductivity, it is preferred that the marker has a boiling point of less than 250° C. (at 1 atm), more preferably less than 200° C.

Depending on the choice of polymer with variable conductivity as explained below, not only alkaline and acidic agents can be used as marker, but also oxidizing and reducing agents. As one example of such markers, mention may be made of silanes having one or two hydrogen atoms bond to the silicon atom. The inventors tested different concentrations of dimethyl phenyl silane as marker in diesel fuel with polyaniline as polymer with variable conductivity, using a method employing evaporation of the marker, and obtained a significant and characteristic change in conductivity over time that distinguished a marked fuel from a non-marked fuel.

Polymer with Variable Conductivity

The polymer formulation used in the present invention contains a polymer with variable conductivity that reacts with the marker present in the liquid to be tested. The conductivity of the polymer with variable conductivity is significantly reduced or increased by the reaction with the marker.

Polymers with variable conductivity typically belong to one of two categories: polymers that in their insulating form contain basic sites and can be made conductive (doped) by means of a reaction with acids, and polymers without basic sites in the main structure that can be made conductive (doped) by means of a reaction with oxidizing agents, such as for example $I_2$, $AsF_5$, $FeCl_3$, Polymers belonging to the first category, once doped, can be brought again in their insulating form (de-doped) by reaction with bases. On the other side polymers of the second category can be reversed to the insulating form (de-doped) by reaction with reducing agents, such as hydrogen, alkali metals, sodium naphthalide etc. The choice of suitable oxidizing and reducing agents can be performed without further difficulty based on the skilled person's general knowledge in view of compatibility with the polymer and the oxidation or reduction potential.

In case the insulating polymer is reticulated after the polymer with variable conductivity has been added to the formulation, the latter should not be able to prevent the reticulation of the former. This can be ensured by the proper choice of components and reagents for reticulation based on the skilled person's general knowledge. Suitable reagents and polymers are well known.

In a preferred embodiment polyaniline in the emeraldine (conductive doped) state can be used. This doped polymer could be de-doped using a basic molecule able to remove protons from the structure (FIG. 9). Optionally it could be possible to restore the conductive emeraldine state by doping, i.e. acidifying, the polymer with a suitable substance. In case of a deprotonation reaction with the marker, the conductive state may be restored by treating the polymer with an acid.

Particularly preferably polymers with variable conductivity are those which can be doped and de-doped by means of a reaction with a base or an acid, or with a reducing and an oxidant agent, respectively, as shown in FIG. 9 for polyaniline. Besides polyanilines other polymers can be used, such as poly(pyrrole)s (PPY), polycarbazoles, polyindoles (the conductivity of which can be changed by suitable oxidizing and reducing agents), and polyazepines (the conductivity of which can be changed by suitable acids or bases). Other examples of conductive polymers that could be used in the present invention include poly(fluorene)s, polyphenylenes, polypyrenes, polyazulenes, polynaphthalenes, polyacetylenes, poly(p-phenylene vinylene), poly(thiophene)s (PT), poly(3,4-ethylenedioxythiophene) (PEDOT)/poly(p-phenylene sulfide) (PPS). As will be readily apparent to the skilled person, the choice of the polymer also influences the choice of the suitable marker, as the marker must be able to change the conductivity provided by the polymer with variable conductivity. Suitable combinations can be found by the skilled person based on routine experiments and taking into consideration the common knowledge about the factors influencing the conductivity of conductive polymers.

The polymer with variable conductivity is typically an essentially linear, non-threedimensionally crosslinked polymer. Suitable variable conductive polymers are commercially available, or can be synthesized by a skilled person using well-known techniques.

Insulating Polymer

As polymer with variable conductivity are difficult to handle and have limited stability when used alone, the polymer formulation employed in the present invention contains an insulating polymer that provides robustness to the formulation and that fixes and retains the polymer with variable conductivity. The insulating polymer is preferably inert according to the definition provided above. Further preferably, the insulating polymer is inert towards the liquid (e.g. fuel) to be tested. Also, the insulating polymer is preferably insoluble or little soluble in the liquid to be tested.

The insulating polymer can be a photopolymer. In the present invention, the term "photopolymer" is used to denote a polymer that is produced by a radical, ionic or non-ionic polymerization process that is initiated by irradiating a polymerizable composition with light, preferably UV light, in order to decompose a polymerization initiator present in the composition to form species (e.g. radicals or cations) that initiate the polymerization reaction.

The type of the insulating polymer is not particularly limited, and any polymer providing physical integrity to the polymer formulation can be used. However, as the liquid to be tested is typically a non-polar hydrocarbon fuel and the marker therein is typically a relatively more polar substance, it is preferable that the insulating polymer contains polar groups. In this case, the marker in the liquid will selectively permeate through the more polar surface of the polymer formulation, which will then facilitate the reaction with the polymer with variable conductivity, causing a decrease or an increase of the conductivity of the polymer formulation.

Suitable polymers thus include homopolymers and copolymers of ethylene and alpha-olefins having 3 to 20 carbon atoms, such as polypropylene or a copolymer of ethylene and propylene. Polymers obtained from monomers having ethoxylated fractions, alcoholic groups, esters, ethers and more in general polar groups are however generally preferred. Preferred examples include acrylate and methacrylate polymers (in the following jointly referred to as (meth)acrylate polymers). A further advantage of (meth)acrylate polymers is that they are typically soluble in selected polar organic solvents, such as MEK or acetone, and can be processed easily in solution or in neat form as hot-melts. Nonetheless, they are insoluble or have only little solubility in the liquid to be tested, e.g. hydrocarbon fuels, which are typically less polar.

The insulating polymer used in the present invention is therefore preferably a homopolymer or copolymer of (meth)acrylate monomers selected from (meth)acrylic acid and alkyl esters of (meth)acrylic acid, such as butyl acrylate, ethyl methacrylate and 2-ethylhexyl acrylate.

Another class of suitable polar insulating polymers are those having poly (alkylene oxide) units, such as poly (ethylene oxide) and/or poly (propylene oxide) units. These include poly(ethylene oxides) such as PEO having a suitable molecular weight of e.g. 2000 or greater, or 10,000 or greater.

A further particularly preferably class of suitable insulating polymers are those formed from precursor compounds wherein more than one (e.g. two, three or four) crosslinkable groups are present. These are preferred in order to increase the chemical resistance of the final polymer formulation to the liquid, e.g. diesel fuel. As one example, the C5 polymer listed in table 4 has a good reactivity with respect to the marker, but also a high permeability to unmarked diesel fuel producing an unwanted resistivity variation.

Among these precursor compounds having more than one crosslinkable group, precursor compounds having a branched structure with several (e.g. 2, 3, 4, or 5) crosslinkable groups are preferable. Examples thereof include polymers obtained from a trimethylolpropane derivative, e.g. 1,1,1-trimethylolpropane triacrylate or trimethylolpropane triglycidyl ether. These include also polymers obtained from these species wherein the acrylate or glycidyl ether crosslinkable groups are provided with more distance from the branching carbon atom, e.g. by providing spacer groups. These spacer groups are preferably polar. Most preferably, the spacer groups are ethylene oxide or propylene oxide units, in particular ethylene oxide units.

Examples of such species include e.g. trimethylolpropane ethoxylated triacrylates of the following formula

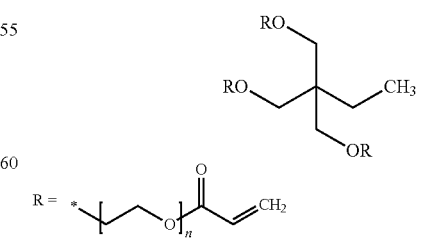

Herein, n is an integer of 1 to 30, preferably 4 to 15. Such compounds are commercially available e.g. from Sigma Aldrich (CAS 28961-43-5).

Another preferred class of insulating polymers are those obtained from poly(akylene oxide)s having one or two terminal (meth)acrylate group, such as poly(ethylene glycol) monoacrylate having a molecular weight of 200-600. Such compounds are commercially available from e.g. Sigma Aldrich.

Polymer Formulation

The polymer formulation employed in the present inventions comprises (or consists of) one or more polymers having variable conductivity and/or one or more insulating polymers, as described in detail above.

The amount of the polymer with variable conductivity in the polymer formulation needs to be sufficient to provide the polymer formulation the ability to vary its electric conductivity when exposed to a proper marker substance. For this purpose, the relative amount of the polymer with variable conductivity is generally 10% by weight or higher, preferably 15% by weight or higher, and more preferably 20% by weight or higher, relative to the total weight of polymer with variable conductivity and insulating polymer.

However, if the amount of the polymer with variable conductivity is too high, the problems thereof as regards stability and processability may have a detrimental influence on the polymer formulation. Accordingly, the amount of the polymer with variable conductivity is typically less than 65% by weight, preferably 50% or less, and further preferably 45% or less, relative to the total weight of polymer with variable conductivity and insulating polymer.

The polymer formulation can be obtained by dissolving the pre-formed insulating polymer and the pre-formed conductive polymer in a suitable solvent, such as xylene, mesitylene, or benzene, mixing the solutions and removing the solvent. In this case, the polymer formulation is a blend of the insulating and conductive polymer. This blend may then be applied to the testing device by conventional means. The polymeric formulation can e.g. be dispensed by spray coating, spin coating or dipping method. In any case, the polymeric conductive blend should be deposited on the walls and/or the floor of the reaction chamber 5.

In order to increase the stability of the polymer formulation and to improve the anchorage of the polymer with variable conductivity in the polymer formulation, it is however preferable to prepare the polymer formulation by providing the pre-formed polymer with variable conductivity and precursor compounds of the insulating polymer, preferably having several crosslinkable groups as outlined above (such as the ethoxylated acrylate species, e.g. the trimethylolpropane ethoxylated triacrylates) in a suitable solvent, such as xylene, mesitylene, or benzene, and in the presence of a photoinitiator. Upon irradiation of the photoinitiator, species (e.g. radicals) are generated, which then initiate the crosslinking of the precursor compounds of the insulating polymer. The insulating polymer precursors then react with each other, thereby providing a matrix of insulating polymer surrounding the pre-formed polymer with variable conductivity. This provides for a better incorporation of the polymer with variable conductivity into the polymer formulation as compared to a blend of polymers. In this case, one should select a photoinitiator that is activated at wavelengths not shielded by polymer with variable conductivity and with a photodecomposition mechanism not inhibited by the presence of the polymer with variable conductivity. Suitable photoinitiators are well known to the skilled person and include for instance Esacure KTO46 and Esacure TPO (available from Lamberti, Italy).

Preferably, the polymerizable composition suitable for forming the polymer formulation, comprising the polymer with variable conductivity, the precursor compound of the insulating polymer (preferably having more than one crosslinkable group, as described above), a solvent and a photoinitiator, is applied to the detection device at the position where the variable conductive strip or layer is to be formed, and is then irradiated with suitable electromagnetic radiation (preferably UV) in order to effect a reaction of the crosslinkable groups, thereby forming a matrix of the insulating polymer surrounding the polymer with variable conductivity. This preparation technique has the advantage that the crosslinked matrix of insulating polymer is formed directly at the place where it is needed, and that further complicated operations can be avoided. Further, in this manner the robustness towards the liquid to be tested can be increased.

One should take care that the insulating polymer precursors and the polymerization reaction is compatible with the polymer with variable conductivity. The inventors found that radical polymerization or crosslinking of acrylate monomers is compatible with polyaniline, as after UV exposure to promote the formation of insulating polymer no resistance increase was observed. The acrylate monomers and the photoinitiator listed in table 4 give good results in term of compatibility with the polymer with variable conductivity.

Further, it goes without saying that the components used in the polymerizable composition for forming the polymer formulation should not interact negatively with the polymer with variable conductivity. This includes the general necessity to avoid basic substances that could neutralize the positive charge of a conductive polymer like polyaniline (see FIG. 9). Similarly it's preferable to avoid acid substances that could promote positive charges localization on an insulating polymer like polyaniline.

If it is intended to use a polymer with variable conductivity by reaction with oxidizing or reducing agents, it is self-evident to the skilled person that substances should be avoided that could promote negative interactions toward the polymer with variable conductivity. For example, if the polymer with variable conductivity is doped with an oxidizing agent, reducing agents should be avoided in the inert polymer formulation and vice versa.

In one embodiment, the polymer formulation comprises a polymer with variable conductivity that changes its conductivity upon reaction with a base, which is preferably a polyaniline in a conductive (protonated) form, and the marker used is a base, e.g. an amine such as trimethylamine. The insulating polymer in this embodiment is a polymer that is not exclusively hydrocarbon-based (such as for instance in the case of polyethylene), but is a polymer that has polar groups along the side chain and/or side chain of the insulating polymer, for allowing easier penetration of the polar marker into the polymer formulation. Such polar groups may be selected from ether groups (—O—), ester groups (—C(O)O—), carbonyl groups (—C(O)—), secondary and tertiary amine groups, amido groups (—C(O)—NH—), amide groups, amino groups, hydroxyl groups, sulfur-containing groups such as (—S(O)—) or (—S(O)$_2$—), sulfonamides, and other polar groups known to the skilled person. In this embodiment, the amount of the insulating polymer is preferably 50% by mass or greater, more preferably 70% by mass or greater of the total of insulating polymer and polymer with variable conductivity, and the amount of polymer with variable conductivity is preferably 15% by mass or greater, but preferably 40% by mass or less. This embodiment can be combined with all other embodiments described herein, such as with the embodiment wherein a device containing a heater element for vaporization of the maker(s) is used, or wherein there is a distillation-type arrangement in the device for separating the marker(s) from the liquid.

Authentication Method and Use of the Polymer with Variable Conductivity

The present invention further encompasses in one embodiment a method for detecting a marker in a liquid, comprising the steps of:

optionally concentrating and/or separating the marker from the liquid;

introducing the marked liquid, a concentrated material obtained therefrom or the separated marker, into a reaction chamber of a detecting device, the reaction chamber containing the polymer formulation with variable conductivity such as to build a path between two conductive pads connected to a resistivity measurement device;

letting the marker react in the reaction chamber with the polymer formulation comprising a polymer with variable conductivity; and measuring the resistivity change of the polymer formulation comprising the polymer with variable conductivity.

In the method of the present invention, the device according to the present invention described above can be used.

In one embodiment of the method for detecting a marker in a liquid according to the present invention, the marker is concentrated in the liquid or separated therefrom. This is preferably be achieved by providing a heater element in the device used, as explained above, to thereby cause evaporation and/or concentration of the marker. Here, the marker first of all vaporizes and is then directed to the reaction chamber, either in vapor form or in condensed form. A higher degree of separation can be obtained if a device containing an element capable of performing a distillation operation is used. This increases the concentration of the marker in the material supplied to the polymer formulation with variable conductivity, which in turn allows reducing the sample size and/or the concentration of the marker in the liquid. While other technologies such as HPCL or adsorbents such as silica gel can also be used, these techniques are less favorable due to the necessity for providing additional components (such as silica gel and/or solvents) that have to be disposed off after the detection test has been performed. Accordingly, if a step of concentrating and/or separating the marker from the liquid is performed, this step is preferably a thermal step consisting of evaporation and optionally condensation of the marker, and is a step that does not require additional components that are consumed or altered during the separation and/or concentration step.

The step of separating and/or concentrating the marker from the liquid is however optional, so that also the liquid as such, without any prior concentration or separation of the marker(s), can be brought into contact with the polymer formulation with variable conductivity, to then determine the resistivity change of the polymer formulation. As the sensitivity of the method is however increased and smaller concentrations of the marker (s) can be used if the concentration and/or separation step is performed, conducting this step is a preferred embodiment of the method of the present invention.

The change in resistivity observed upon contact of the marker, or a liquid containing it, with the polymer formulation having variable resistivity can then be exploited for authentication purposes. For instance, a liquid may only be classified as genuine and authentic if it conforms, within certain boundaries, to pre-defined expectation value ranges with respect the observed resistivity change (total or over a given time).

EXAMPLES

The inventors performed several experiments in order to identify suitable de-dopant molecules (markers) and to assess the sensitivity and accuracy of the method/device. The markers evaluated in the experiments on different conductive polymeric formulations are listed in table 1 and 2; and the further possible markers suitable for the application to carry out the invention are listed in table 3.

In parallel, the influence of the insulating polymer on the absorption of the marker in the fuel has been evaluated. The insulating polymer strongly influences the ability of the conductive polymer to decrease its conductivity. The inventors prepared and studied different polymeric formulations listed in table 4. The markers listed in table 1 have been tested depositing a 2 µl drop on the conductive polymer which is positioned as a path (or "bridge" which does not need to be suspended over any substrate) between two conductive pads present on a PCB having a distance of 1 mm. The electric signal is brought out by means of electric tracks also present into the PCB and the resistance (or conductivity) measurement is made by means of an external tester.

After collecting the starting resistance value of the polymer formulation, the resistance variations after 1 and 5 minutes contact between the pure liquid and the polymer formulation were recorded.

Each marker listed in table 1 had a very strong de-dopant effect on the doped polyaniline present in the polymer formulation. The diesel fuel alone however does not produce relevant resistance variations with respect to the tested markers. Notwithstanding the insulating properties of diesel fuel, it is interesting to observe that, once in contact with the conductive polymer, diesel is unable to produce a sensible increase of electrical resistance. This happens as a consequence of the physical and chemical characteristic of the polymer formulation, in particular the insulating polymer. The polymer C11 for example has a very high polarity that promotes the permeability of the markers, while preventing the permeation of the less polar diesel fuel.

In table 1 and 2 are also listed some solubility data of the tested additives into the diesel fuel.

Figure 3:
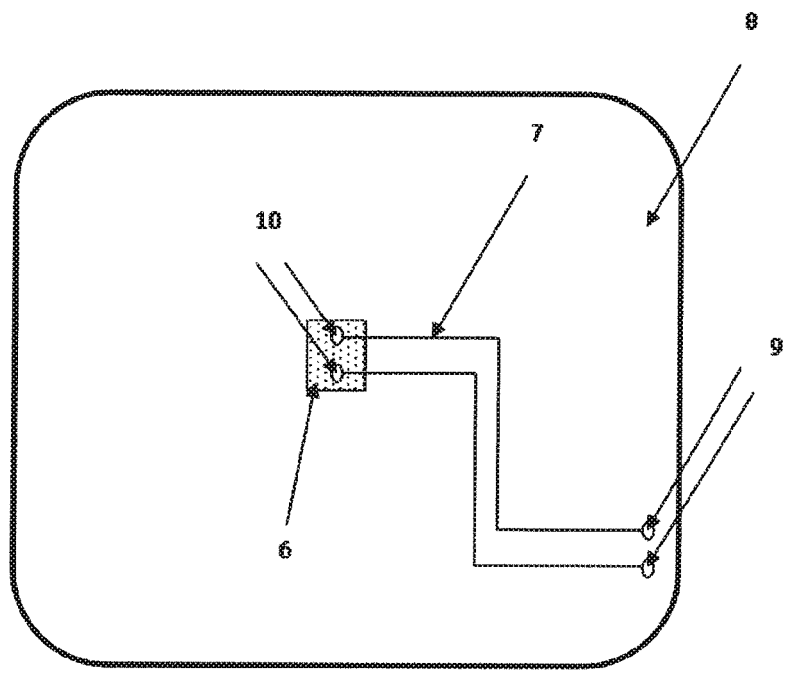

The polymerizable compositions have been prepared in a glass shielded jar, by means of a scale and simple magnetic stirrer. The mixing procedure has been executed at room temperature for 3 hours. Once finished the dilution process, 20 µl of each formulation has been deposited on electrical PADs 10 of a PCB 8 having the structure described in FIG. 3. After the deposition performed by means of a Meyer bar or a microsyringe, the formulation is dried at room temperature in 2 minutes; the formulation is polymerized in nitrogen atmosphere by using a UV mercury lamp with an emission spectra in UVA and visible range. The total energy is preferable higher than 800 mJ/cm$^2$ on UVA range.

The conductive polymer formulation 6 produces a conductive path (bridge) between the two conductive PADs 10 which are 13 mm far. The electrical resistance is detected by means of a tester connected to two pins 9 which are connected, by means of electric tracks 7, to the conductive polymer 6.

Figure 2:
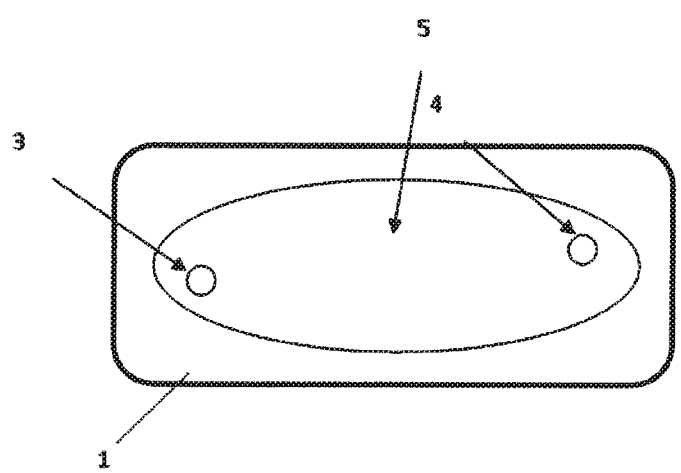

After the UV exposure, using alignment reference points present on the PCB surface 8, the microhydraulic 5 in FIG. 1 or 2 is put on top to the PCB. The polymer formulation is contained in the microhydraulic 5. This conductive element is able to react with the marker in the fuel, leading to an increase in resistance.

The fuel is injected into device through the inlet hole 3 and air can escape from the outlet hole 4; in FIG. 1 the device contains an injection chamber 2 where the liquid is collected before moving to the reaction chamber 5.

The microhydraulic in FIGS. 1 and 2 could be made by plastic material like PE, HDPE, Kapton, PTFE, COC and COP. This material can be bonded to the PCB by means of a UV or thermal curable glue deposited on the microhydraulic walls 1; alternative bonding techniques like heat bonding, solvent bonding, laser welding etc could be used as well.

After the bonding step the device is ready for the analysis. The analysis of the fuel could be performed keeping the PCB at different temperature; the temperature may influence the permeation of the marker into the polymer 6 and the kinetic reaction between marker and conductive polymeric fraction (polyaniline).

Figure 4:
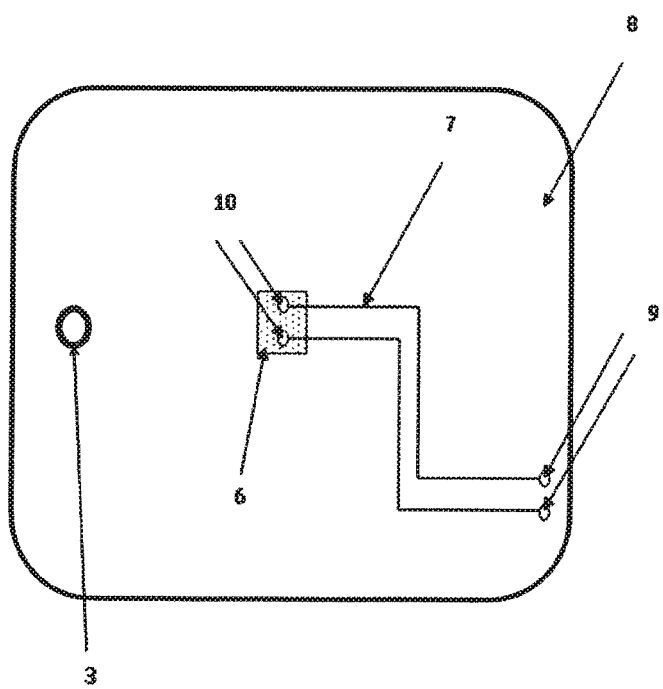
Figure 5:
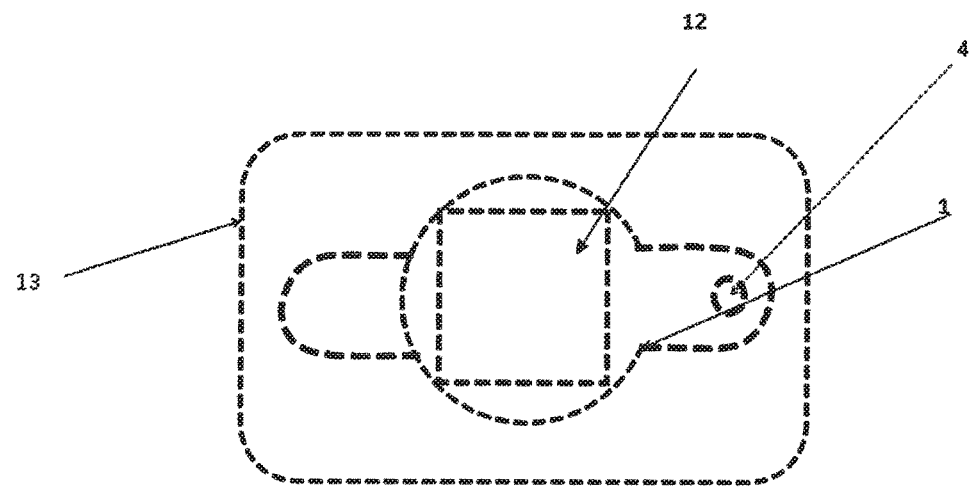
Figure 6:
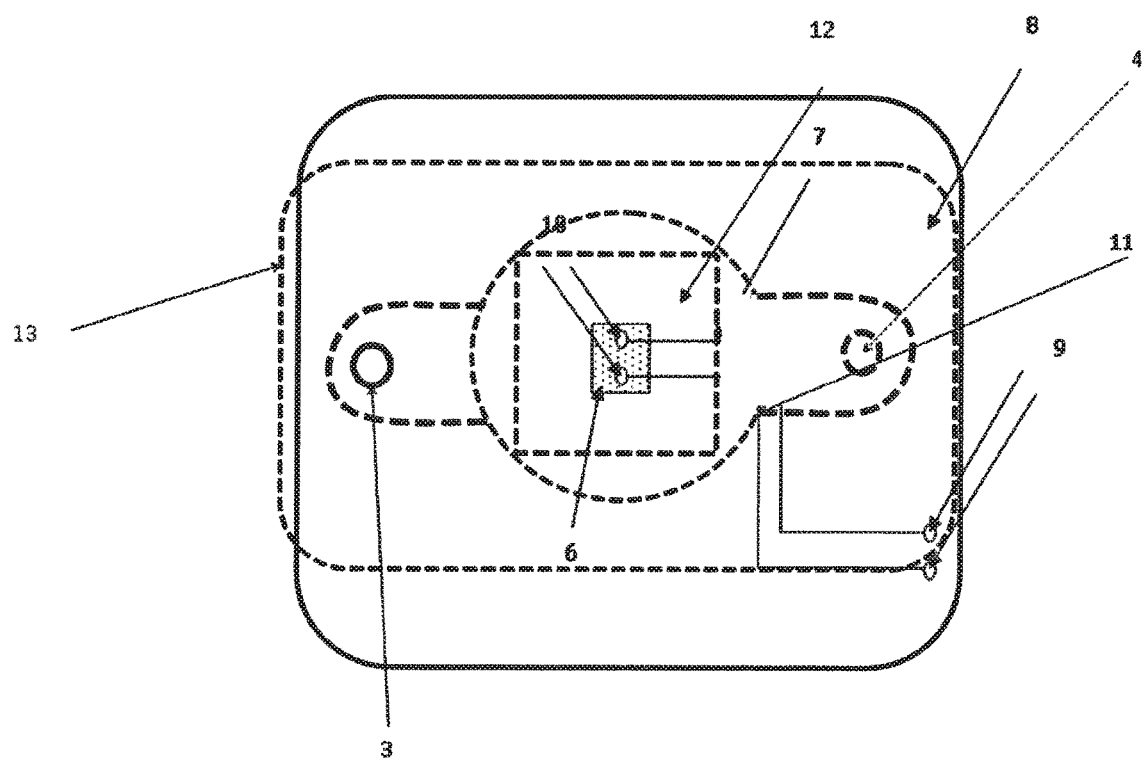

In FIGS. 4, 5 and 6 it is described an alternative device configuration that can preferably provide a higher sensitivity: it is able to generate and detect vapors and generally volatile fractions of the marked fuel. This configuration and the related methodology concentrate the marker contained into the fuel, increasing the final output signal.

In this device there is a heater element (12) (e.g. a simple electrical resistor) on the bottom layer (FIG. 5); this bottom layer (13) could be a simple PCB having an outlet hole (4). On the top layer (FIG. 4) there is a microhydraulic circuit 1 which can be bonded to the bottom device; this channel conveys the liquid to the heater element (12) where it is heated up to a specific temperature next to the boiling point of the marker, with a controlled rate. The vapor having a concentrated fraction of marker will contact the conductive sensors 6; the conductive polymer 6 will react with the concentrated marker giving a characteristic electric resistance variation, that is function of the molecular properties of the vaporized marker. Optionally it could be useful to introduce an external heating source on the top layer which contains the polymeric formulation in order to avoid condensation phenomena of fuel vapors.

The fuel may contain more than one marker with different boiling points. In principle different markers should be detected separately as the temperature grows up. The device preferably works at atmospheric pressure due to the outlet hole 3.

The configuration described in FIG. 6 preferably provides a signal having less background noise (due to contact between polymer and not-reactive fuel fraction) and in principle is able to detect very low concentrations of markers. Finally this method increases the selectivity by introducing a crossing evaluation of a physical property of each marker molecule (the boiling point) in parallel with the reactivity of marker (function of molecular weight, number of reactive functionalities, permeability into the polymer, dissociation constant of the salt of protonated marker with anion of polyaniline) with respect to the conductive polymer.

Figure 7:
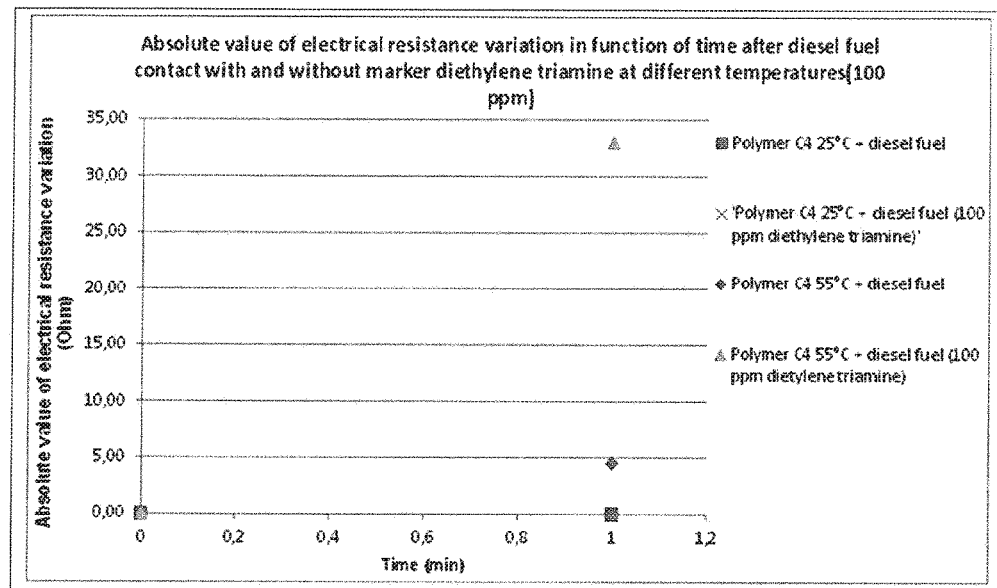
Figure 8:
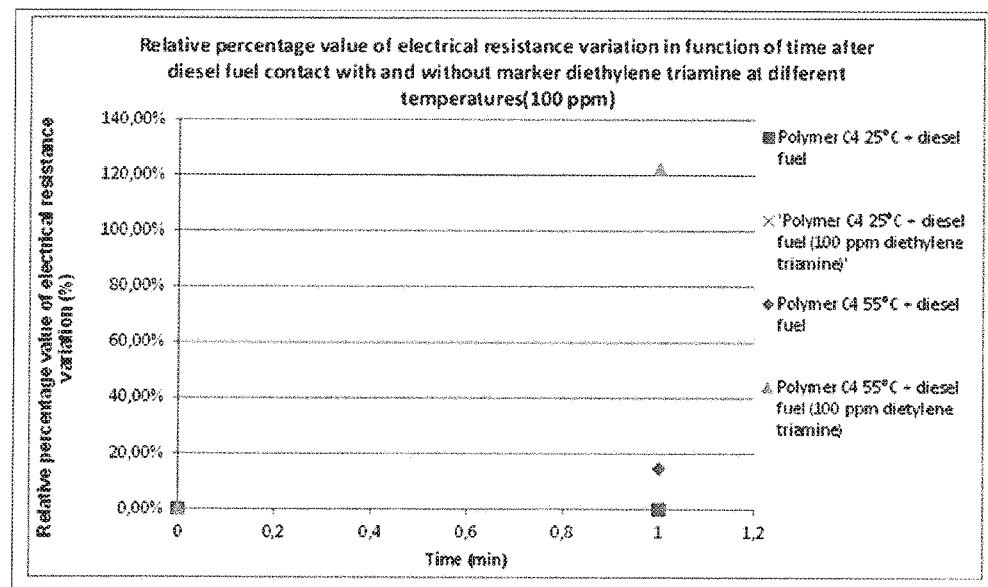
Figure 14:
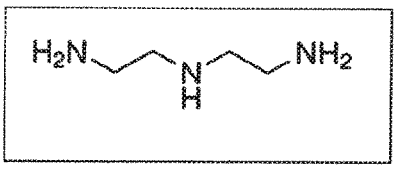
Figure 15:
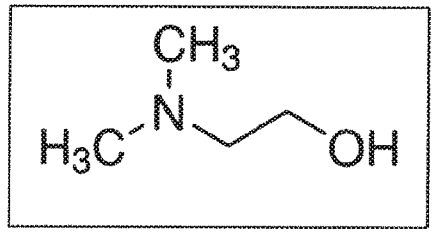
Figure 16:
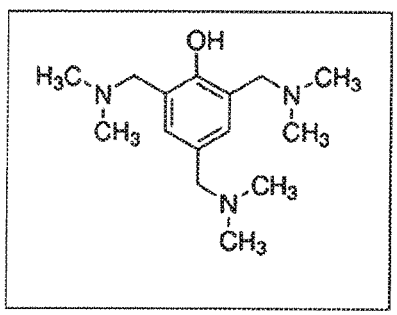
Figure 17:
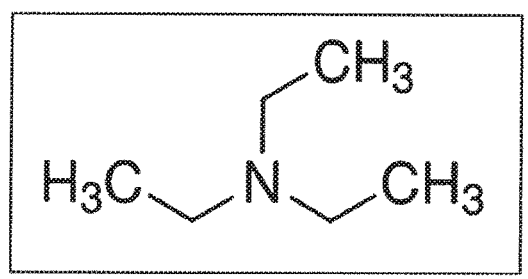
Figure 18:
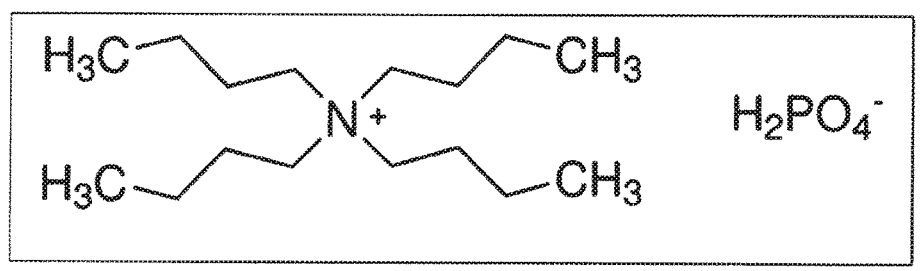
Figure 19:
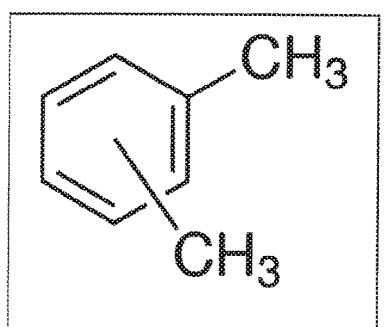
Figure 20:
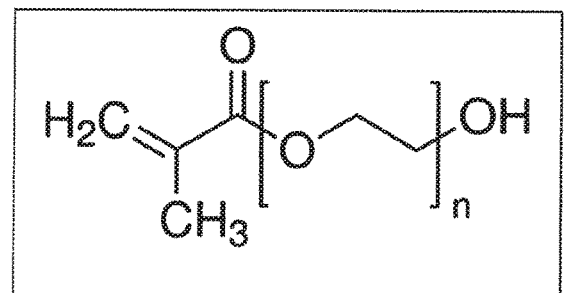
Figure 21:
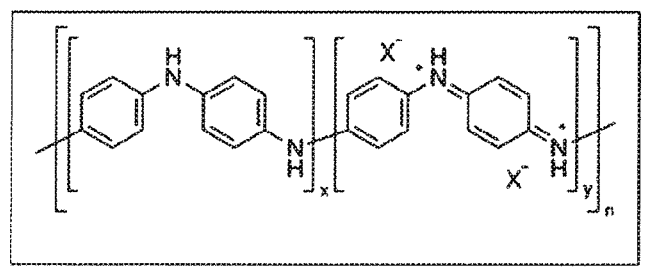
Figure 22:
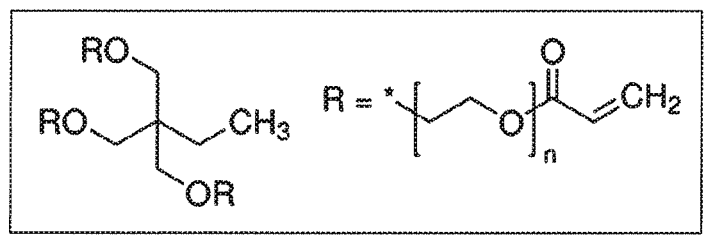
Figure 23:
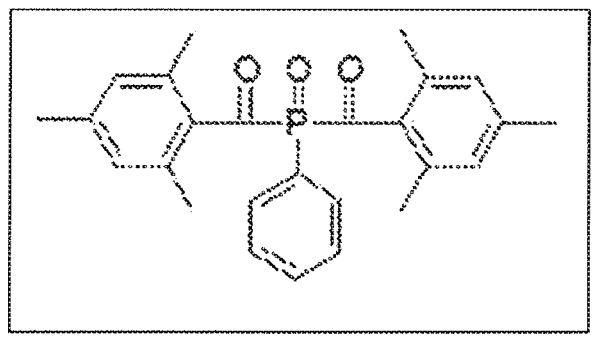

FIGS. 7 and 8 show the resistance variation after 1 minute of contact between conductive polymer and fuel containing 100 ppm of diethylene triamine (molecular structure represented in FIG. 14) in absolute value and relative percentage value of the formulation C4 (listed in table 3) as a function of temperature.

Increasing the temperature from 25° C. to 55° C. the resistance of conductive polymer increases too: this physical phenomenon is due to the increase of liquid absorption into the polymer. At 25° C. after one minute no significant fuel permeation inside the polymeric blend takes place, so resistance variations can be observed neither with marked nor with unmarked fuel. Increasing the temperature the liquid permeate more easily into the polymer: the insulating fuel without additive produce a resistance increase of about 110% after 1 minute at 55° C. but introducing into the fuel 100 ppm of diethylene triamine the resistance increase of about 220% in respect to the initial resistance value. At 55° C. there's a higher reactivity of the amine compound to doped polyaniline, in respect to the experiment at 25° C.

It has been executed comparative experiments between polymeric formulation C4 and C5 at 55° C. It seems that formulation C4 is more selective to the de-dopant diethylene triamine additive in respect to C5; the resistance variation of C5 at 55° C., after contacting fuel, seems to be less related to the presence of diethylene triamine.

Thanks to the colour difference of the polyaniline in doped and de-doped state, in principle it could be possible to introduce also an optical detector in order to collect a UV-Visible spectral variation after the contact with the marked fuel.

TABLE 1

List of marker tested on C11 polymer formulation

| | Maximum evaluated concentration of marker soluble into diesel fuel | Resistance T0 (kOhm) | Resistance after 1 minute (kOhm) | Resistance after 5 min (kOhm) |
|---|---|---|---|---|
| Triethyl amine (Sigma-Aldrich); | ≤10000 ppm | 0.536 | 4700 | 5400 |
| Jeffamine T-403 (Huntsman) | ≤1000 ppm | 0.54 | 70 | 6200 |
| N-butyldiethanolamine (Sigma-Aldrich) | <100 ppm | 1.72 | 5900 | 3100 |
| Silquest A-1100 (Momentive) | ≤1000 ppm (solution stability problem after few days) | 0.387 | 4400 | 1670 |
| Dimethyl amine in THF(2M) (Sigma-Aldrich) | ≤1000 ppm | 0.814 | 2200 | 19000 |
| 2,4,6 Tris (dimethylaminoethyl) phenol (Sigma-Aldrich) | ≤100 ppm | 0.45 | 3900 | 12000 |
| Dimethylethanolamine (Sigma-Aldrich) | <100 ppm | 0.55 | 3000 | 8000 |

TABLE 1-continued

List of marker tested on C11 polymer formulation

| | Maximum evaluated concentration of marker soluble into diesel fuel | Resistance T0 (kOhm) | Resistance after 1 minute (kOhm) | Resistance after 5 min (kOhm) |
|---|---|---|---|---|
| Diethylenetriamine (Sigma-Aldrich) | <100 ppm | 0.75 | 2900 | 9000 |
| Diesel fuel (Shell) | / | 0.41 | 0.67 | 0.9 |

TABLE 2

List of marker tested on C10 polymer formulation

| | Maximum evaluated concentration of marker soluble into diesel fuel | Resistance T0 (kOhm) | Resistance after 1 minute (kOhm) | Resistance after 5 min (kOhm) |
|---|---|---|---|---|
| Triethyl amine (Sigma-Aldrich); | ≤10000 ppm | 0.56 | 4300 | 4000 |
| Jeffamine T-403 (Huntsman) | ≤1000 ppm | 0.52 | 11500 | 32000 |
| N-butyldiethanolamine (Sigma-Aldrich) | <100 ppm | 0.52 | 3200 | 2500 |
| Silquest A-1100 (Momentive) | ≤1000 ppm (solution stability problem after few days) | 1.9 | 6150 | 1400 |
| Dimethyl amine in THF(2M) (Sigma-Aldrich) | ≤1000 ppm | 0.44 | 4.7 | 2.4 |
| 2,4,6 Tris (dimethylaminoethyl) phenol (Sigma-Aldrich) | ≤100 ppm | 3.3 | Out of scale | Out of scale |
| Dimethylethanolamine (Sigma-Aldrich) | <100 ppm | 0.5 | 4000 | 8000 |
| Diethylenetriamine (Sigma-Aldrich) | <100 ppm | 0.48 | 3000 | 11000 |
| Tetrabutylammonium phosphate monobasic (Sigma-Aldrich) | <100 ppm | Not tested | Not tested | Not tested |
| Diesel fuel (Shell) | / | 1.77 | 7.3 | 9.2 |

TABLE 3

List of possible additives

Diethylamine
Dimethylamine
Benzyltrimethylammonium hydroxide
N,N-Diisopropylmethylamine
1,8-Diazabicyclo[5.4.0]undec-7-ene
Piperidine
2,2,6,6-Tetramethylpiperidine
1,5,7-Triazabicyclo[4.4.0]dec-5-ene
n-Butyllithium
2,6-Lutidine
1-propylbutylamine
2-Aminoheptane
Cyclohexylamine
2-cyclopropyl ethyl amine
Dipropylamine

TABLE 4

Polymerizable compositions for forming polymer formulations (all values in wt. %)

| | C4 | C5 | C10 | C11 |
|---|---|---|---|---|
| Trimethylol propane ethoxylated triacrylate (MW428) (Sigma-Aldrich) | 45.76 | 0 | 0 | 0 |
| Trimethylol propane ethoxylated triacrylate (14EO/3OH) (MW912) (Sigma-Aldrich) | 0 | 0 | 32.1 | 0 |
| PEG monoacrylate(MW360) (Sigma-Aldrich) | 0 | 45.76 | 0 | 0 |
| Glycerol 1,3-diglycerolate diacrylate (Sigma-Aldrich) | 0 | 0 | 0 | 22.13 |
| Polyaniline (emeraldine salt) (Sigma-Aldrich) | 22.03 | 22.03 | 36.6 | 25.09 |
| Xylene (Sigma-Aldrich) | 27.13 | 27.13 | 27.4 | 48.2 |
| Esacure KTO46 (Lamberti) | 0 | 0 | 3.9 | 4.58 |
| Esacure TPO (Lamberti) | 5.08 | 5.08 | 0 | 0 |

The compounds used in the Examples are as follows:

Trimethylol propane ethoxylated triacrylate (MW428): An acrylate with medium polarity. The compound is a trifunctional monomer able to reticulate by means of a radical process. The resulting insulating polymer provides chemical, physical and mechanical resistance to the polymer formulation, facilitating the marker extraction from the fuel and the permeation into the polymer.

PEG monoacrylate (MW360): An acrylate polar monofunctional monomer able to polymerize by means of a radical process. The resulting polymer provides high polarity to the polymer formulation and increases its flexibility in consequence of the decrease of reticulation density.

Polyaniline (emeraldine state): A polymer with variable conductivity. The polymer could have, in presence of positive charges neutralized by anions onto the molecular structure, an inherent conductivity due to the presence of conjugated double bonds. This polymer with variable conductivity could show reduced conductivity as a consequence of a reaction with a basic marker and could show increased conductivity as a consequence of reaction with an acid marker.

Xylene: organic solvent used into the formulation in order to dilute the ingredients and reduce the final viscosity.

Esacure TPO: radical photoinitiator able to promote, once exposed to UV-Vis radiation, a radical reaction of acrylate monomers. This photoinitiator is able to absorb the radiation in spite of the polyaniline presence which has an intense absorption in UV-Vis range.

Advantageous ingredients listed in table 3 are:
Polyaniline (emeraldine state) in order to provide the polymer formulation with variable electric conductivity;
Trimethylol propane ethoxylated triacrylate (MW428) or PEG monoacrylate (MW360) or Glycerol 1,3-diglycerolate diacrylate in order to provide chemical and mechanical resistance to the polymer formulation in addition to the increase of marker absorption ability;
Esacure TPO in order to initiate the reticulation or polymerization of the acrylate monomers.

Figure 27:
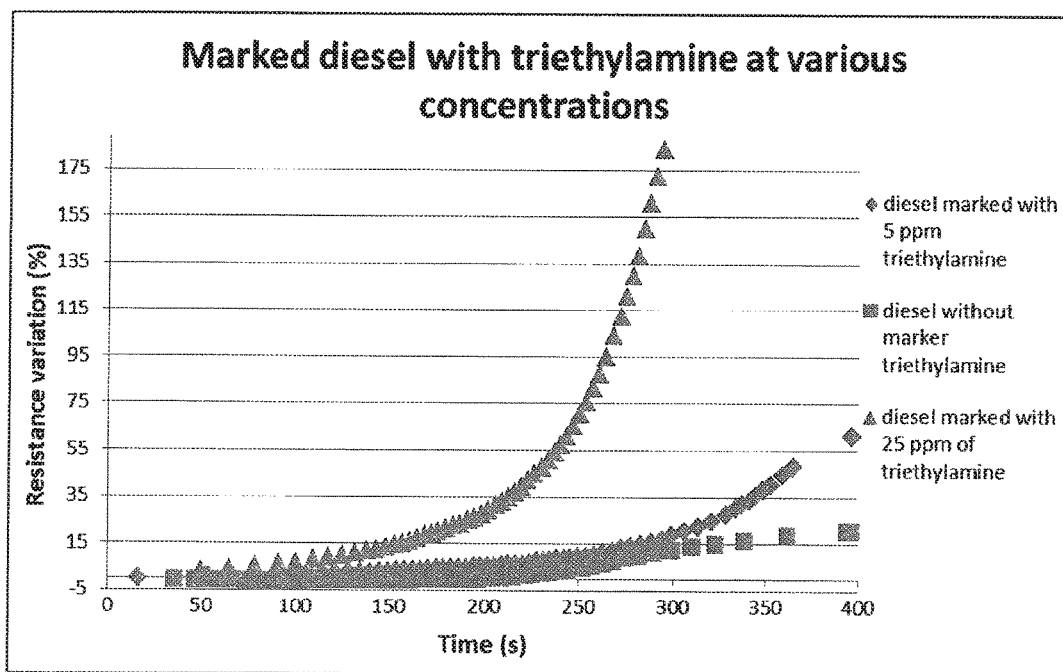

An additional experiment has been conducted in order to evaluate the influence of the marker concentration on the observed resistivity variation. FIG. 27 shows a plot of % Resistance variation in function of the time in order to evaluate the concentration of the marker on the resistivity variation over time.

The experiment has been executed following the listed steps:
1. Injection of 5 cc of diesel fuel marked with various concentrations of triethylamine into the reaction chamber at room temperature;
2. Heating of the reaction chamber by means of a heating element, with a ramp of 0.5° C./s, up to 100° C.;
3. Maintaining of the system at 100° C. at least for 1 minute;
4. Cooling of the system and collecting of the Resistance variation (%) in function of time and temperature of the fuel.

As shown in FIG. 27, the observed resistivity variation over time depends, under otherwise identical conditions, on the concentration of the marker. Hence, the authentication method of the present invention allows for determining the authenticity of a liquid, as a counterfeiter not only has to identify the marker species, but also has to adjust the amount thereof in order to mimic the response of the genuine liquid. The method thus is also able to detect laundering processes, such as dilution of authentic fuel with non-authentic fuel.

The markers proposed in this invention can be difficult to be identified once dissolved into the fuel without specific or authorized equipment. At the same time their detection can be relatively easy performed using a conductive polymer. The marker and the polymer with variable conductivity contained in the polymer formulation can react with specific kinetics, which allows also recognizing the reactive species, thereby providing a valuable and reliable tool for verification and authenticity check purposes, especially in the context of liquids.

The invention claimed is:

1. A detection device for detecting a marker in a liquid, comprising:
   a reaction chamber, provided with a polymer formulation with variable conductivity building a path between two conductive pads connected to a resistivity measurement device, wherein the conductive polymer formulation is configured to react with a marker to thereby change its resistivity;
   a heater element configured to heat and to evaporate the marker dissolved in the liquid, and
   a housing for enclosing the reaction chamber and a housing cover comprising a printed circuit board, wherein said conducting pads are arranged on said printed circuit board facing the reaction chamber.

2. The detection device according to claim 1, wherein the polymer formulation with variable conductivity comprises a polymer with variable conductivity and an insulating polymer, wherein the amount of polymer with variable conductivity is 10% by weight or higher, and less than 65% by weight, relative to the total weight of polymer with variable conductivity and insulating polymer.

3. The detection device according to claim 1, wherein the polymer formulation is formed by photocuring a photocurable polymerizable composition comprising a conductive polymer, precursor compounds capable of forming an insulating polymer and a photoinitiator.

4. The detection device according to claim 2, wherein the insulating polymer comprises a polar group in the polymer main chain and/or side chain.

5. The detection device according to claim 1, further comprising an element capable of performing a distillation operation.

6. The detection device according to claim 1, wherein said housing comprises a heat conducting part on a side opposing said conductive pads, wherein a volume is arranged between said heat conducting part and said conductive pads.

7. The detection device according to claim 1, wherein the reaction chamber is coated with the polymer formulation with variable conductivity.

8. The detection device according to claim 1, wherein the polymer with variable conductivity is configured so that a marker diluted in the liquid at a concentration smaller than 150 ppm generates a resistivity change greater than 30% on the polymer with variable conductivity, relative to the resistivity prior to contact with the marker.

9. The detection device according to claim 3, wherein the photocurable polymerizable composition comprises:
   15 to 50% wt of a polymer with variable conductivity;
   20 to 60% wt of a (meth)acrylate monomeric or oligomeric species able to generate, after a polymerization reaction, an insulating polymer;
   1 to 10% wt, of a radical photoinitiator;
   0 to 60% wt of an organic solvent, preferably xylene;
   based on the total weight of the photocurable composition.

10. The detection device according to claim 2, wherein a weight ratio of insulating polymer/variable conductive polymer in the polymer formulation with variable conductivity, respectively in the polymerizable composition used to produce the polymer formulation with variable conductivity, is between 0.5 and 2.5.

11. The detection device according to claim 1, wherein the polymer formulation with variable conductivity is configured to change resistivity upon contact with a marker capable of abstracting a proton therefrom.

12. A system comprising:
A detection device according to claim 1;
a fuel as said liquid;
a marker dissolved in the fuel with a concentration<150 ppm.

13. A method for manufacturing a detection device according claim 1 comprising the steps of:
depositing a polymerizable composition comprising a) a polymer with variable conductivity, b) precursor compounds capable of forming an insulating polymer, and c) a photoinitiator on the walls and/or on the floor of the reaction chamber and/or on the conductive pads; and
irradiating the polymerizable composition, preferably with UV radiation.

14. The method according to claim 13, wherein a weight ratio of insulating polymer/polymer with variable conductivity in the polymerizable composition used to produce the polymer formulation with variable conductivity is between 0.5 and 2.5.

15. A method for detecting a marker in a liquid, comprising the steps of:
concentrating and/or separating a marker from a liquid, which includes evaporation of the marker from the liquid;
introducing the marked liquid, a concentrated material obtained therefrom or the separated marker, into a reaction chamber of a detecting device, the reaction chamber containing a polymer formulation with variable conductivity to build a path between two conductive pads connected to a resistivity measurement device;
letting the marker react in the reaction chamber with the polymer formulation comprising a polymer with variable conductivity;
measuring a resistivity change of the polymer formulation comprising the polymer with variable conductivity, and wherein the detecting device is the device according to claim 1.

16. The method according to claim 15, wherein the liquid is a fuel, the marker is a diluted marker, dissolved in said fuel, and the insulating polymer is a polymer having a polar group.

17. A method for verifying the authenticity or genuineness of a liquid comprising taking a measurement of a resistivity of a polymer formulation with variable conductivity or of a polymer with variable conductivity that comprises the polymer formulation with variable conductivity using the device of claim 1, both before and after a liquid.

18. The detection device according to claim 4, wherein the polar group is selected from the group consisting of ether groups, ester groups, carbonyl groups, secondary and tertiary amine groups, amido groups, amide groups, amino groups, hydroxyl groups, —S(O)— and —S(O)$_2$—.

19. The detection device according to claim 1, wherein the liquid is a fuel.

20. The detection device according to claim 8, wherein the resistivity change is greater than 50%.

21. The detection device according to claim 8, wherein the resistivity change is greater than 100%.

22. The detection device according to claim 9, wherein the polymer with variable conductivity is polyaniline, or monomers or oligomers able to generate a polymer with variable conductivity as a consequence of a polymerization reaction.

23. The system of claim 12, wherein the marker dissolved in the fuel is an amine.

24. The method of claim 16, wherein the marker is an amine.

* * * * *